US010842378B2

(12) United States Patent
Verma (10) Patent No.: US 10,842,378 B2
(45) Date of Patent: Nov. 24, 2020

(54) DIGITAL HEALTHCARE PRACTICE SYSTEM FOR DIGITAL CITIZENS

(71) Applicant: Shiv Prakash Verma, Cedar Knolls, NJ (US)

(72) Inventor: Shiv Prakash Verma, Cedar Knolls, NJ (US)

(*) Notice: Subject to any disclaimer, the term of this patent is extended or adjusted under 35 U.S.C. 154(b) by 363 days.

(21) Appl. No.: 15/880,530

(22) Filed: Jan. 26, 2018

(65) Prior Publication Data

US 2018/0160907 A1    Jun. 14, 2018

(51) Int. Cl.
*A61B 5/00* (2006.01)
*G16H 80/00* (2018.01)
(Continued)

(52) U.S. Cl.
CPC ........ *A61B 5/0022* (2013.01); *A61B 1/00016* (2013.01); *A61B 1/00034* (2013.01); *A61B 1/00096* (2013.01); *A61B 1/00188* (2013.01); *A61B 1/04* (2013.01); *A61B 1/0684* (2013.01); *A61B 1/227* (2013.01); *A61B 1/233* (2013.01); *A61B 1/24* (2013.01); *A61B 5/0205* (2013.01); *A61B 5/02055* (2013.01); *A61B 5/6898* (2013.01); *A61B 5/725* (2013.01); *A61B 5/7232* (2013.01); *A61B 5/7465* (2013.01); *A61B 7/00* (2013.01); *A61B 7/008* (2013.01); *A61B 7/02* (2013.01); *A61B 7/026* (2013.01); *A61B 7/04* (2013.01); *G06Q 10/101* (2013.01); *G06Q 30/04* (2013.01); *G06Q 50/22* (2013.01); *G16H 40/67* (2018.01); *G16H 50/20* (2018.01); *G16H 80/00* (2018.01); *A61B 5/0008* (2013.01); *A61B 5/01* (2013.01); *A61B 5/0402* (2013.01); *A61B 5/04012* (2013.01); *A61B 5/12* (2013.01); *A61B 5/145* (2013.01); *A61B 5/441* (2013.01); *A61B 5/4552* (2013.01); *A61B 5/486* (2013.01);
(Continued)

(58) Field of Classification Search
CPC .................................................. A61B 5/0024
See application file for complete search history.

(56) References Cited

U.S. PATENT DOCUMENTS 9,642,529 B1 * 5/2017 Siddiqui ................ G16H 50/20
2014/0058755 A1 * 2/2014 Macoviak ........... G06F 19/3462
705/3
(Continued)

*Primary Examiner* — Matthew F Desanto (57) ABSTRACT

A web server based digital healthcare practice system to provide digital transformation of physician practice to twenty first century. Physician can provide in home remote patient examination using a smart pocketable integrated multi function device to perform all head to toe examination similar to his office. And can perform computer assisted cardio and pulmonary, abdominal sound diagnosis, ear, nose, throat analysis, and skin analysis from remote to pin point accurate ailment and write prescription to pharmacy, and bill insurance companies. Invention allows patients seek health care 24/7 in state, out of state, out of country and use in state insurance company to pay for the services. A virtual reality model of physician is available for normal everyday ailments.

The smart pocketable integrated device used is remotely controlled by the physician and has smarts build to make it very user friendly and is wirelessly connected to an application running on a smartphone/tablet/laptop which is connected to physician server.

1 Claim, 5 Drawing Sheets

(51) Int. Cl.
*G16H 40/67* (2018.01)
*A61B 1/00* (2006.01)
*A61B 1/04* (2006.01)
*A61B 1/227* (2006.01)
*A61B 1/233* (2006.01)
*A61B 1/24* (2006.01)
*A61B 5/01* (2006.01)
*A61B 7/00* (2006.01)
*A61B 7/02* (2006.01)
*A61B 7/04* (2006.01)
*A61B 5/0402* (2006.01)
*A61B 5/04* (2006.01)
*A61B 5/0205* (2006.01)
*A61B 5/12* (2006.01)
*G06Q 30/04* (2012.01)
*G06Q 10/10* (2012.01)
*G06Q 50/22* (2018.01)
*A61B 1/06* (2006.01)
*G16H 50/20* (2018.01)
*A61B 5/145* (2006.01)

(52) U.S. Cl.
CPC ........... *A61B 5/7435* (2013.01); *A61B 7/003* (2013.01); *A61B 2503/04* (2013.01); *A61B 2560/0209* (2013.01); *A61B 2560/0257* (2013.01); *A61B 2560/0431* (2013.01); *A61B 2562/0204* (2013.01); *A61B 2562/046* (2013.01); *Y02A 90/22* (2018.01); *Y02A 90/26* (2018.01)

(56) References Cited

U.S. PATENT DOCUMENTS

| | | | |
|---|---|---|---|
| 2015/0281231 A1* | 10/2015 | Ganesan | H04L 63/0853 455/411 |
| 2016/0344710 A1* | 11/2016 | Khan | H04L 63/061 |
| 2017/0329922 A1* | 11/2017 | Eberting | G16H 10/60 |
| 2018/0000367 A1* | 1/2018 | Longinotti-Buitoni | G06K 9/00892 |
| 2018/0090229 A1* | 3/2018 | Sanyal | A61B 5/0022 |
| 2018/0226158 A1* | 8/2018 | Fish | G16H 80/00 |
| 2018/0253954 A1* | 9/2018 | Verma | G08B 21/043 |
| 2018/0277238 A1* | 9/2018 | Boesen | A61B 5/0024 |
| 2019/0046039 A1* | 2/2019 | Ramesh | G16H 80/00 |
| 2019/0133445 A1* | 5/2019 | Eteminan | A61B 5/002 |
| 2019/0198167 A1* | 6/2019 | Durlach | A61B 5/002 |

* cited by examiner

DIGITAL HEALTHCARE PRACTICE SYSTEM FOR DIGITAL CITIZENS

BACKGROUND OF THE INVENTION

1. Field of Invention

This invention relates to a physician's practice system in a digitally connected world with digital patients of today with a smartphone/tablet/laptop. The system allows patient to consult and treated with his primary care physician while at home, office and travelling.

Providing timely, cost effective, and quality health care to all citizens have been a paramount goal everywhere in the world. The patient and the primary care physician relationship has been the pillar of the most medical practices in the world. Trust in a physician strongly related with the recovery. And the primary care physician acts as a first point of contact for a patient's wellness and this relationship continues for long time, and sometimes for the life of the patient and physician. As population grew, relationship between a patient and a doctor has grown from doctor visiting home of a patient in 1960's—as portrayed in 'Marcus Welby MD' TV series—to present day of making an appointment to see a physician at a clinic. This has created a big demand of trained physicians to cater the need of growing population, and demands more services with increasing longevity numbers, from forties to eighties after the invention of antibiotics and modern medicines. It has also created a big divide between metro versus rural areas of the country with respect to timely and quality of health care in the US. It has also created a similar divide between the developed and developing world. It takes weeks to months to get an appointment with a physician in certain part of country and rural areas. And this shortage is getting acute everywhere.

The growing population of family with both spouse holding full time jobs puts an added pressure when someone in the family gets sick. One of them has to take off from work to take a sick to family primary care physician. And sometimes they have to wait for hours if the physician has a fully booked calendar.

Young children, aging population living at home, disable, and special needs care people have to be driven to their family primary care physician, PCP, for minor illness. This further adds stress on the life of working couple and effected people.

Most families travelling out of state and out of country end up paying higher medical bills as most of insurance plans only cover in state medical care, and pay significantly less if you visit out of network physicians and hospitals in the country. And it is almost nothing if you travel overseas. Senior citizens who chose to move to warmer climate states from cold climate states, during winter would end up paying higher medical bills. They can't get care from their family primary care physician at home state.

Senior citizens travelling overseas are at jeopardy if they get sick as most medical supplemental plans don't cover out of state or out of country medical cost. Seniors who chose to live overseas during their retirement years have no access to their medicare provided services, although they continue to pay for Medicare supplemental insurance.

The use of technology to solve medical problems is not new to our society. Tele medicine has been around since 1950's. It has been used to serve rural population but did not get much foot on the ground due to operation cost, poor quality and missing patient, physician family bond.

The need to monitor and assist a patient out at home has been long felt, once physicians stopped visiting our homes. The U.S. Patents No: 2001/0056226 A1 by Richard Zodnik et. al., U.S. Pat. No. 6,014,432 by David Rodney is about a patient medical monitor that can allow a health care provider to remotely monitor and assist a patient using analog networks of the time. However it did not get any attention as it did not address many issues relating running a practice to maintaining patient records, insurance billing, etc. All this increases burden of cost of running a private practice.

There has been lot of technological development in last two decades. Internet has evolved from a 2.4/4.8/9.6 kb/s hybrid network of 1990's to all digital super highway offering global connectivity to all. Wireless networks have evolved from analog voice networks to very high speed digital broadband networks offering global digital connectivity.

Mobile computing has evolved from a 24 pounds Osborne portable computer with no communication connectivity to less than two pounds Laptops with all medium of connectivity and processor at least 1000 times powerful than the processor's of 1981.

The mobile phones has evolved from a brick phone (bulky analog phone) with voice only capability to today smartphone, with very powerful processors with high speed global connectivity to broadband wireless networks, and features rich, as face recognition, speech input and many more. It is not impossible that whole world will use these smart phones to conduct all their daily business not in distant future, as technology as well as demand will drive the cost curve down to make it affordable to all.

There is next wave of innovation happening in the medical devices. Wearable devices have been around for few years which monitor your heart rate, activity rate, blood pressure etc. and can connect with smart phones, Internet of Things (IOT) is going to drive price curve low with more functionality for these devices.

In last five years, tele-health services have been offered to customers at home using laptop/smartphone to talk to a physician, who is remote and unknown to a patient. This model defies the age old practice of sacred doctor to patient personal relationship which is built on trusts and care in the community you live in. These tele-health services are like going to a physician who only exists on the screen away from home without any personal bond a patient is used to.

The hospitals and private practitioners are silos when it comes to patient care information technology and services. They have integrated their backend operations like billing, hospital run radiology centers & Test Labs, patient record sharing, with the physicians having practice privileges with their hospital system. Patient can access their medical raw test charts on their smartphone, and can send message to their primary care physician.

The present invention transforms the medical practice to $21^{st}$ century. It allows client/patient all the benefits of today's and evolving technology. And maintains patient-physician's model practiced globally. It solves all the issues a patient faces in getting timely, quality and cost effective medical care. It allows the patient 24/7 care of their PCP while at home or travelling, and help PCP to transform practice into digital practice using all the technological development to increase, productivity and profitability.

BRIEF SUMMARY OF INVENTION

A Web Server based digital health care practice system which allows patient 24/7 remote office visit or in person office visit to a family physician, virtual reality, VR, family physician or any other physician from home or anywhere in the world. The system allows patient to visit a physician office, hospital, pharmacy, test labs, radiology centers, in state, out of state, and out of country and get reimbursed by the home insurance company. The system comprise a smart compact pocketable integrated wireless digital device with plurality of body function monitoring such as pulmonary and cardiac sounds, abdominal sounds, body temperature and ear, nose and throat pictures. The device is controlled by an application running on the patient's smartphone/tablet/laptop connected through Internet to the physician's web server and it allows a physician to conduct head to toe examination remotely from office the same way as if the patient is in the office using a smartphone, tablet, laptop, desktop.

The invention has number of servers at the physician's office which perform functions needed in a paper less practice. A Server which handles secure communications with the remote patient's Application and physician's Application using crypto technology, authentication using digital face and age, digital voice and finger print recognition, password with one time password matching, patient's and physician's application management, interaction with other servers—e.g. hospitals, insurance companies, test labs, radiology centers, state and federal government, global settlement and reconciliation, and patient's home location, HLR, and visiting patient's location, VLR, management.

Another server is used for voice and video conferencing, virtual reality, VR, based physician's examination scripts for various common ailments, voice and video text, and email messaging and text alerts.

And another server which performs real time mathematical analysis of the patient's body functions signals to assist a physician with diagnosis, and picture and sound records of patient's body during examination. It acts like a medical assistant which gets better as it adaptively learns with more data. It also has a prescription assistant to suggest possible medicine for the patient, a symptom checker with virtual reality examination using physician's video script to run a virtual reality based physician examination on the remote patient. Another server is used to maintain physicians' calendars for patient's remote and in office visits, home and visiting patient's billing application, pharmacy application, insurance billing, global patient's bill reconciliation, data analytic tools.

The invention has a data base system to store, retrieve, and archive all the raw data, and all these servers are connected together with a local area network and a router connected to broadband internet. All these functions can be resident on a multi core single server for a small practice to separate servers as listed, or in cloud.

The invention uses a Physicians' application running on a physician smartphone/tablet/laptop/desktop, which allows a physician to give examination in his office or remote location to a patient using smart portable pocketable device of this invention. Physician terminal can be on the physician office or remotely connected to the server through Internet. Physician uses voice or touch activated commands to control functions of the smart pocketable device, connected via a wireless link to patient application running on the patient's smartphone/tablet/laptop. The application displays picture of body parts, and it allows a physician to give remote examination to a patient. The physician can get patient's text and email alerts, get assistance from the mathematical analysis server, control calendar, and send prescription to a pharmacy and patient, also send referrals to other physician's in state, arrange voice and video conference with other specialists, and send patient's HLR and referrals to global settlement server for out of state healthcare, and generate billing code for the examination service.

The system in invention has patient's application running on a smartphone/tablet/laptop connected to Internet, which controls over a wireless link, the smart pocketable digital device, based on commands received from the physician application during examination over the Internet. And this application is used by the patient for registration with the physician web server, authentication by the physician web server using face and age recognition, voice and finger print recognition, password and one time password matching. The patient also uses it to set appointment for in home virtual or office visit, emergency alert to the physician, prescription refills, referrals, text and email to physician. It is also used to look at dash board of the health chart, upload histogram of blood pressure and sugar level monitoring data to physician's server for proactive medical care. It displays picture of body parts during examination, video and voice conference with the physician.

The invention has a global data base server for billing, authentication and settlement reconciliation among participating service providers for healthcare to allow interstate and out of country medical care to visiting patient's, and billing insurance company for health care service through their home physician, hospitals, Test Labs, pharmacy.

The smart compact pocketable integrated digital device has built in plurality of functions for body function examination and monitoring. It has a digital camera for examining eyes, ear and throat, and a digital thermometer. It has a digital MEMS barometric sensor to measure patient's height, and motion detection of the device to guide the patient at the optimum position during heart, lung, abdominal auscultation. The device has eight dual plate digital MEMS microphone for body sound listening, where each dual plate digital MEMS microphone is remotely turned on/off by an application running on the physician smartphone/tablet/laptop using touch or voice input. The device has a digital processor to process speaker independent keyword voice command and acoustic processing, and a separate digital signal processor for functions such as-filtering heart sound during lung sound auscultation etc., and a microcomputer with embedded firmware to control all these functions and communicate with the patient application running on the smartphone/tablet/laptop, and a power management and battery charging circuitry and a bluetooth wireless device, and an OTG connector for charging the Li-Ion battery and connecting other health related devices.

Eight dual plate digital MEMS microphones of this device are arranged in two concentric circles—with four microphones in each circle—in the size of diaphragm of a classic stethoscope, and needs no pressing of diaphragm or switching of bell like in a classic stethoscope and can be used for infants and adults for auscultation.

The smart device of this invention has built in speaker independent key word recognition. It is controlled by an application running on a smartphone/tablet/laptop by touch or voice activation by the remote physician. It also has a pictorial view of human body organs on smartphone/tablet/laptop application to position the device at the appropriate place for auscultation and examination during remote physician examination. This picture is shown on patient and physician application smartphone/tablet/laptop simultaneously and controlled by the physician by voice or touch command to the physician application running on smartphone/tablet/laptop.

The smart pocketable integrated device of the invention uses a position guiding algorithm using microphone volume, device motion, and height detected by barometric pressure sensor, to optimally position the device at the auscultation point on human body. And it turns organ's picture on application screen from read to green. During the device movement sound signal going from device to the physician's server is substituted with the silence sound and sound is only recorded and listened by the server and physician after the green signal is displayed.

During auscultation the physician application running on the smartphone/tablet/laptop displays picture of eight microphones of the patient's organ monitoring device at the remote site, which physician can turn on/off with touch or voice to listen the best quality of sound. The picture will turn microphone from red to green when on.

Embedded firmware of the smart device in this invention device can be remotely upgraded with added features for body sound analysis, EKG and ECG analysis, throat, tongue, nose, skin and ear analysis to further assist the virtual reality physician, medical assistant and physician.

The invention of this system allows virtual reality, VR, physician examination to a remote patient using pre-prepared video scripts for common ailments using physician virtual reality scripts video, medical assistant, prescription assistant, symptoms manager, and thus giving feel of an examination given by the real family physician the patient is used to.

The HLR and VLR function or similar feature in each participating service provider server, and global settlement server for authenticating visiting patient and payment settlement between home and out of state/country service provider allows a patient to seek healthcare anywhere in the world. A settlement network, similar to interbank network e.g. Visa-net, of participating service provider is envisioned in the invention.

In the invention, the physician, nurse practitioner or on call physician can provide remote patient care from anywhere and don't have to be in the physician's office.

The present invention system is applicable to all healthcare related practices where medical assistant and virtual reality script are changed to reflect new field of practice.

DETAILED DESCRIPTION OF THE INVENTION

Figure 1:
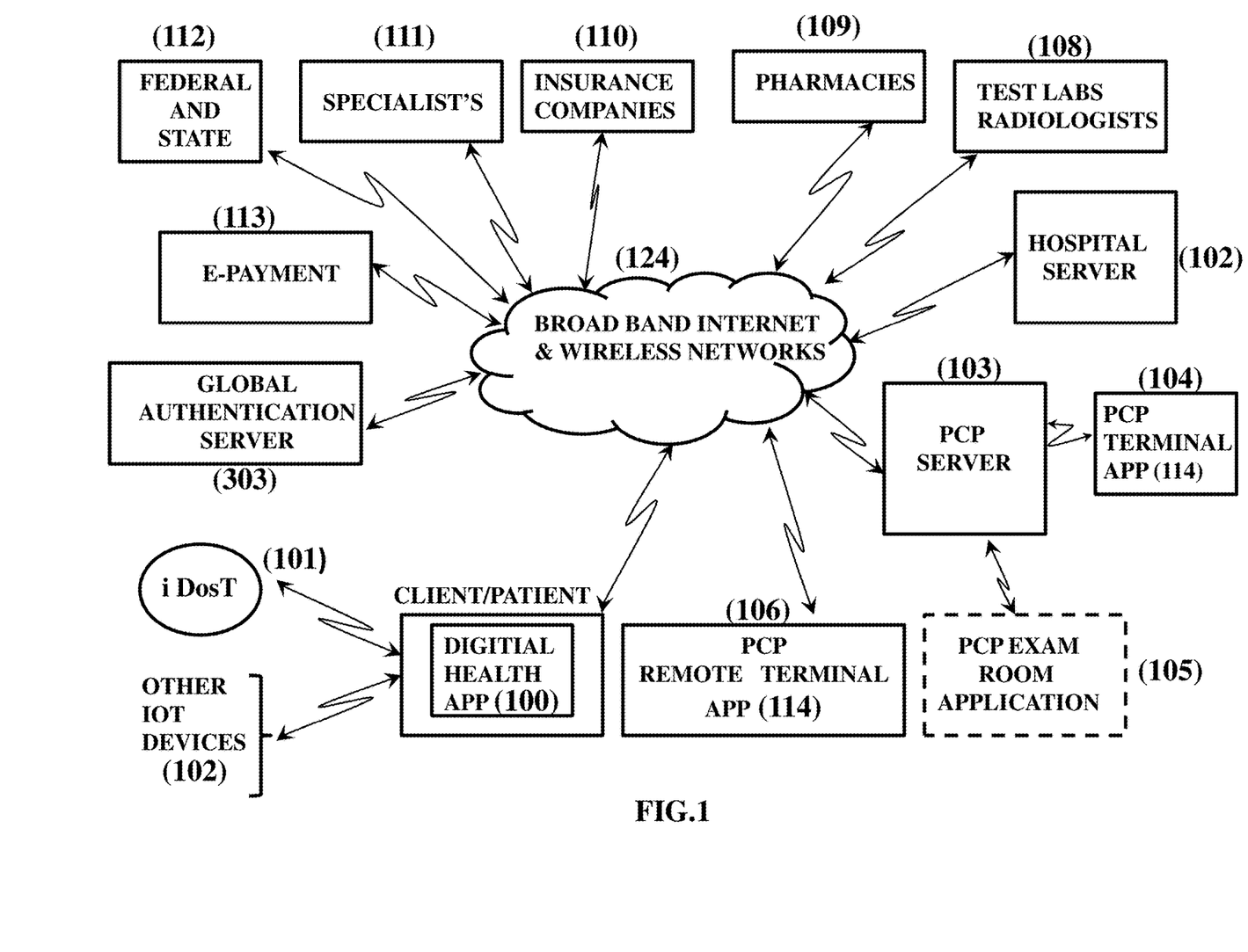
FIG. 1 shows the invention's block diagram of web based digital health care practice system using at patient's home, a smart pocketable integrated device, iDosT, wirelessly connected to a patient's application running on a smartphone/tablet/laptop, connected over Internet to a Primary Care Physician Server with a Physician application running on smartphone/tablet/laptop for remote office and in office visit.

FIG. 1 shows a block diagram of the digital Health Care practice System of this invention. It uses a Smart Device (101) with integrated Digital otoscope, stethoscope and temperature, iDosT. Patient uses this device during physician consultation from home or office. Smart Device (101) communicates with Client/Patients App (100) running on a smartphone, tablet or laptop. This application communicates over a secure link with the Web Based Physician Server (103) over the broadband internet (124). The Physician Server (103) communicates with the servers of Insurance Companies (110), Pharmacies (109), Federal and State Agencies (112), Test Labs and Radiologists (108), Hospital (107) and E-payment system (113). The Physician Terminal (104) and (105) are, connected to the Server (103). Each examination room will have its own laptop running Physician App (114). The whole System of invention allows paper less digital health care practice including patient billing and insurance reconciliation. It supports remote Physician Terminal (106) using a laptop, smartphone or tablet. Physician Terminals are also located in the examination rooms and at other physician's office desk. The remote terminal can be a physician away from the office, another physician substituting during off hours. The iDosT can be used both at patient's home and physician's office. The system in this invention can be used by any specialists in the medical field. The invention is focused on Primary Care Physician (PCP) in the description but it is envisioned that the all the features of the invention is applicable to other practicing specialists e.g. Cardiologists, dermatologist etc. The medical assistant part in the physician's server, is changed depending upon the specialty, and Physician App (114) and Patient App (100) get enhanced to reflect additional protocol followed in the specialty.

Figure 2:
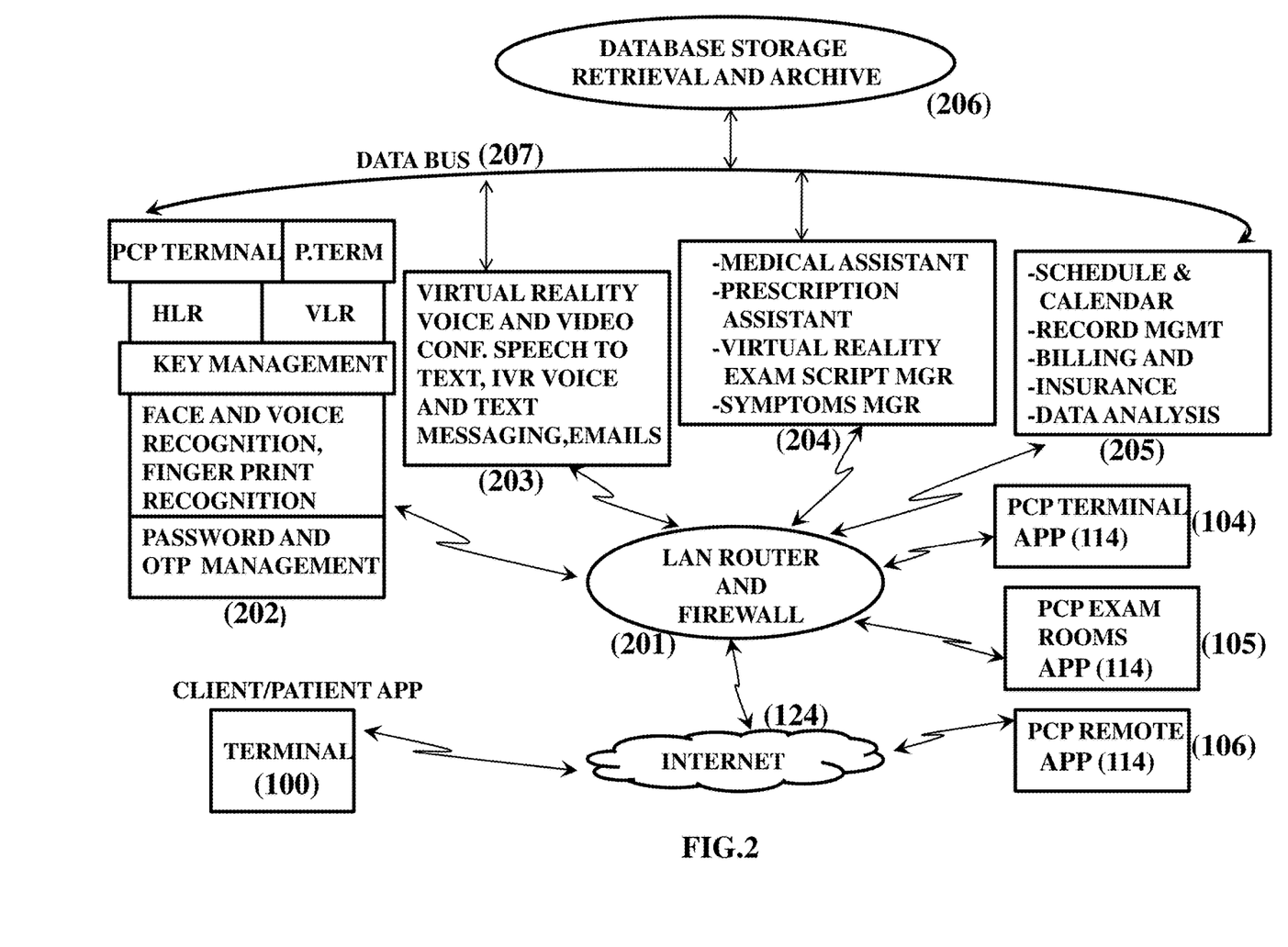
FIG. 2 shows block diagram of the server functions at the Primary Care Physician's location as envisioned in the invention.

The physician's server details is given in FIG. 2. The Server (202) handles the PCP Terminal (114) and Patient Terminal (100) App. It also maintains the Home Location Register, and Visitor Location Register Information of the patient. HLR keeps patient name, unique identification number, home location address, mobile number, insurance information, social security number, picture, voice print, Fingerprint, and unique password. The VLR holds similar information for out of state or another country's authorized patients visiting to see the physician. The Server assigns a temporary unique Id number after authenticating this patient from global settlement Server. Managing the secure communications is also handled in this server. This Server (202) also handles all authentication functions of—face, age, voice, fingerprint, recognition, password (OTP) and its validation. The Server (203) handles all media related functions such as video conference, voice conference, virtual reality video, playing Interactive Voice Response (IVR), voice, video and Text message, email functions.

The Medical Assistant Server (204) is used by the physician to help affirm the diagnosis by using analytical tools like pattern matching, data analytic, auto correlation techniques well known in communication systems. These techniques are used on the information received from patient's iDosT and comparing it with the stored samples of a infected person in the patients age group. Auscultation in medicine is a physical examination method that allows drawing conclusions on patient's state of health based on the sound produced by internal organs. The key drawback of this method is the subjectivity of physician's assessment of acoustic data. Furthermore this also depends on how good is a physician ability to perceive high sounds, and distinguish tones and intonation, given up to 80% of adults have an ear for music, but only 12-15% of them have musical memory. It is also known that the acuity of male and female start going down between age of 32-35 years and 38-40 years respectively. It is also known that the height of a physician professional strength and optimal combination of experience, knowledge, and professional skills fall on the age 35-40 years—the period of time, when human sensing organs start losing their acuity. The use of up-to-date Medical Assistant Server (203) with iDosT producing acoustic signal generated by the patient's cardiovascular, bronco pulmonary, abdominal, organs and also conducting mathematical analysis of these sounds in order to produce objective conclusion on patient's state of health greatly reduces chances for in-correct diagnostics. Computerized lungs sound analysis as diagnostic aid for the detection of abdominal sound is well documented in a paper by checkly et. al published by Science Direct in Jun. 14, 2011. The Medical Assistant Server (203) also conducts analysis on the pictures of patient's ear, throat, and skin to assist physician with the correct diagnoses. The system stores all possible infection related pictures related to ear, throat and skin in the database (206), And (203) performs mathematical pattern recognition or matching algorithms to assist the physician. It can also operate on the data received on patient's tests conducted by the outside labs such as—CBC, Lipid panel, ECG, blood pressure and A1c reading etc. All this data is used by the Server (203), to alert physician any medical condition changes pro actively. All the data is displayed on the Patient App (100) as well as on Physician App (104) in dashboard format using data analytic tools of (205). A physician can use this alert to order further tests and visitation by the patient. Some of the functions of medical Assistant can be implemented in the iDosT (101), patient App (100), PCP App (114), and in the Server (203).

In the invention, the remote patient can also get an examination of common ailments using a virtual reality, VR, based family physician, and patient may not notice if it's the real family physician. The Virtual Reality exam has in it pre-recorded script for common ailments on Server (204). This script manager with symptoms manager looks at the physician calendar to see patients wishing to get a remote visit fall under the script it manages. It will set up the video call to the patient and will go through the script to examine patient while virtual reality driver in (203) will orchestrate the physician's video at each step. At the end of script it will use medical Assistant to diagnose the ailment, and Prescription Assistant to prescribe medication for the ailment and generate a billing code for insurance. The VR script can always be used by the physician during off hours emergency calls.

The Server (205) maintains the calendar for the physicians. The patient can access this calendar to get on the calendar giving the symptoms of ailments for in home or at the physician's office visit. The calendar would show only the available slots. In case of emergency and in home visit the patient can also check to see a Nurse Practitioner's calendar on duty if the physician's calendar is fully booked for the day. Patient App (100) can access other physician's calendars too. Patient can also initiate an emergency alert through App (100) which is posted on the physician's remote smartphone/tablet/laptop (106) running App (114) or Terminal (104) (105). The Server (205) handles patients care co-pay, billing to the insurance companies using Electronics Health Record (EHR) Compliant format. It can communicate with Federal and State Agencies (112), Hospital Server (107), and Servers of other specialists (114). The physician can arrange a video conference with a Specialist (111) on the hospital panel to discuss patient care related issues. Server (205) will support all E-payment platforms (113), for patient to pay bills online.

The Data base Server (206) hosts all the data needed to support the practice. All the Servers share this data base and make use of tools provided to store, retrieve and archive information. All the Servers are connected through a LAN and a Router with Firewall, (201). This router is connected to the Broadband Internet (124), and to PCP Terminal (104), (105), (106). All the servers can be a single multi core server or multiple servers at PCP site or hosted in the cloud.

iDosT (101), is an integrated device with the functions of smart Digital otoscope, stethoscope, thermometer and more. It's a pocketable compact rechargeable battery operated device and works with the Client/Patient Terminal App (100), medical Assistant Server (204), PCP Terminals App (114). The physician with its App (114) can give the iDosT voice command through App (100) to send temperature, blood pressure, cardio and bronco pulmonary, abdomen sound, and nose, ear and throat pictures for examination. Each voice command shows on the Patient App (100) a picture of the body organ where App (114) also allows for a physician to use touch on the PCP App (114) to send command to Patient App (100) and iDosT (101). This completely eliminates any confusion at the remote end for the patient. And there are no switches to be pushed by the patient at the remote location for examination. The iDosT (101) is remotely configured in its modes by the PCP App (114) and has full control of the patient examination as if the patient is in the office. The physician can remotely control the digital filter and directional characteristics of iDosT microphones. There is no Bell or Diaphragm for patient to play in this invention. The iDosT (101) detects the motion of the device and substitutes sound with silence until motion stops to avoid confusion to the physician and medical Assistant App running. After examining of vital signs data, the physician can prescribe a medicine and sends prescription to the patient's pharmacy, and a copy to the patient. PCP App (114) supports this. After patient signs off, the App (114) generates a insurance billing code which PCP clicks with touch, and sends to the Billing Server (205). Intent of the invention is, total paperless transformation of the physician's practice.

Each patient uses App (100) on the smartphone/tablet/laptop to register on the physician website. App (100) uses a highly secured link to communicate with the physician's server. Using this App (100) the patient creates an individual/family accounts with each minor children. A unique number is assigned to each registered patient with all information stored in the HLR Server (202). HLR has all the information needed for billing and authentication for a patient. Patient App (100) uploads all the information needed to generate and validate authentication, to the PCP Server (103) including home GPS Location, and App (100) uses this authentication information to get access to all the service offered by the physician through Server (103). This HLR number is used as a key to identify all the records stored in the database (206) related to a patient. The patient can schedule a remote visit or in office visit to see the physician. And insurance company gets billed for each remote virtual and office visit by the physician, and patients pay co-pay as per prescribed fee in the insurance company plans. This allows a patient to seek physician care from home, and away from anywhere in the world. The patient's physician can help the patient while travelling out of state, country and this further reinforcing the patient to physician relationship.

Figure 3:
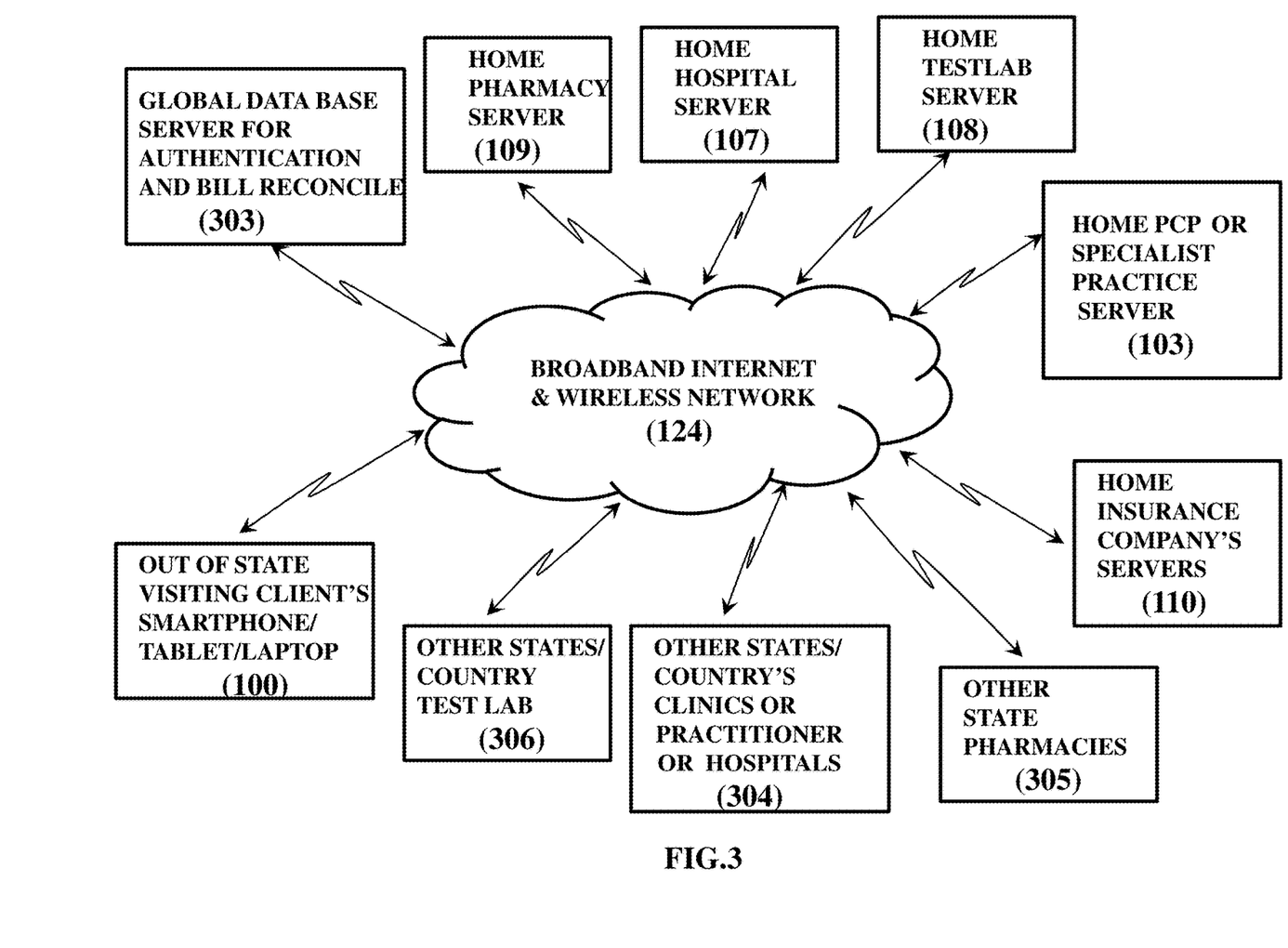
FIG. 3 shows block diagram of web server based digital health care system for patient to get healthcare interstate and other countries using Global database server for authentication and bill settlement using home insurance plan.

FIG. 3 shows a block diagram of the invention to allow a patient seek healthcare in a out of state or country visiting clinics or physicians' offices or hospitals, as most of the insurance companies only pay for the services billed by the in state physicians, Test Labs, pharmacies and hospitals. A Global Data Base Server (303) is used for authentication, bill reconciling among various service providers across the state and country. This server performs all the functions needed to provide a patient medical care across the world. It signs up various service providers in various states, countries for payment settlement terms. And the servers of these providers are connected to Server (303) over a secured link. It is envisioned in this invention that service providers will sign up to provide the patient needing their services. Invention envisions a health net, similar to interbank network like Visa-Net or roaming settlement agreement among international wireless or landline, mobile data or phone service providers. Server (303) can be centralized or distributed as the need grows. The settlement model will depend on the service type and could be cost—plus or type of service e.g. physician visit, tests, surgery, hospital care etc.

A patient visiting away from the home state or in a different country will first use smartphone/tablet/laptop App (100) to get in remote contact with the home PCP Server (103). After the remote virtual visit the physician can advise if the patient needs to see a local physician in the area. The home PCP sends the HLR ID with the patient's current GPS location to the Server (303). The Server (303) looks from its database a participating physician in the area and sends alert to the participating physicians with the visitor information with a temporary ID number to be used in its VLR server. It also sends an alert to the patient with the physician's website information for scheduling remote or in office visit. The patient uses this temporary ID, VLR, to get access to the Clinic Practitioners Website (304) to schedule in office visit. The Visiting Server (304) will send billing information to Global Database Server (303) with its service code ID. The server (303) sends this information to home PCP Server (103) for it to bill insurance company for this health care service. The Server (303) will reconcile this payment to Server (304) based on the service agreement and patients only pays co-pay to the out of state physician. The Server (303) handles settlement between the Out of State/Country Pharmacy (305) and in State Pharmacy (109) if patient needs prescription filled. Server (303) handles settlement between the Home Hospital (107) and out of state/country Hospital (304). It also handles reconciliation of payment between the out of state hospitals and home hospital for visiting patient services. A similar arrangement is made between the participating home Test Labs (108) and out of state/country Test Labs by the Server (303). Home PCP (103), Home Hospital (107), Home Pharmacy (109) and Home Test Labs (108) bill to the local insurance company for patient's services as a home state service. And Server (303) does all the settlement between all the parties.

Figure 4:
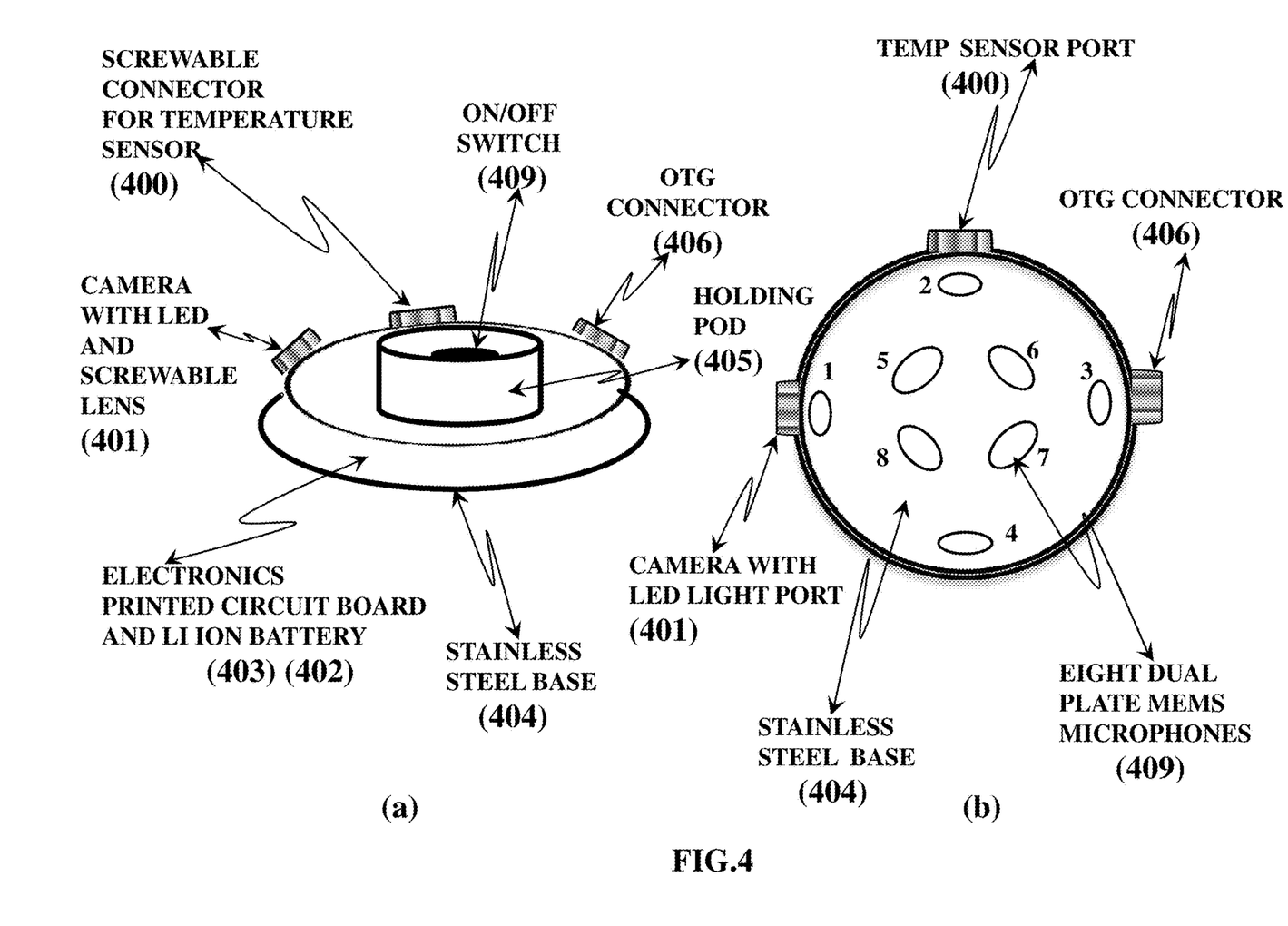
FIG. 4 shows top and bottom view of iDosT physical design

FIGS. 4(a) and (b) give a pictorial view of integrated Digital otoscope, stethoscope and Temperature, iDosT (101), used in the invention. This invention allows a physician to give a patient head-to-toe examination in a remote as well as in office environments. It allows a physician to listen to patient's cardiac and pulmonary sounds, abdomen sounds, look at the ear, nose, eyes and throat, measure height. It also connects to other Bluetooth compatible wireless devices such as ECG, Blood pressure Monitor, etc. It also communicates with USB based medical and fitness related devices.

As shown in the FIG. 4(a) of the invention, iDosT, in its preferred embodiment, is approximately size of the diaphragm side of today's stethoscope. The bottom is a stainless steel base with holes for eight dual plate MEMS Digital Microphone (409). All the electronics, microphones, and connectors are mounted on a single Printed Circuit Board, PCB, (403) The temperature sensor connector is a screw on type which makes contact with Microcomputer's (500) ADC inputs, where a cone shaped temp sensor is crewed to it. A Digital Camera (401) and LED assembles is mounted to the edge of the iDosT's PCB (403). It is housed in a screwable opening, which allows a cone shaped lens to be placed when needed to look at ear, nose, throat and eyes. The LED intensity is remotely controlled by the PCP App (114) or Patient App (100). An OTG connector (406) is used to connect other devices with USB/OTG support. All the electronics is mounted on a PCB (403) with all eight Dual MEMs digital microphones. A LI-ION Battery (402) is housed on the top of PCB (403), and whole assembly is closed with the round holding pod (405) with ON/OFF switch (409). The OTG (406) is also used as a charging connector for the device. The base plate uses a health grade stainless steel. FIG. 4(b) shows the bottom of iDosT with eight MEMS dual plate digital microphones mounted in two circles. The inner circle can be used to listen to body sound of children and infants. All eight microphones are used in listening to body sounds in adults.

Figure 5:
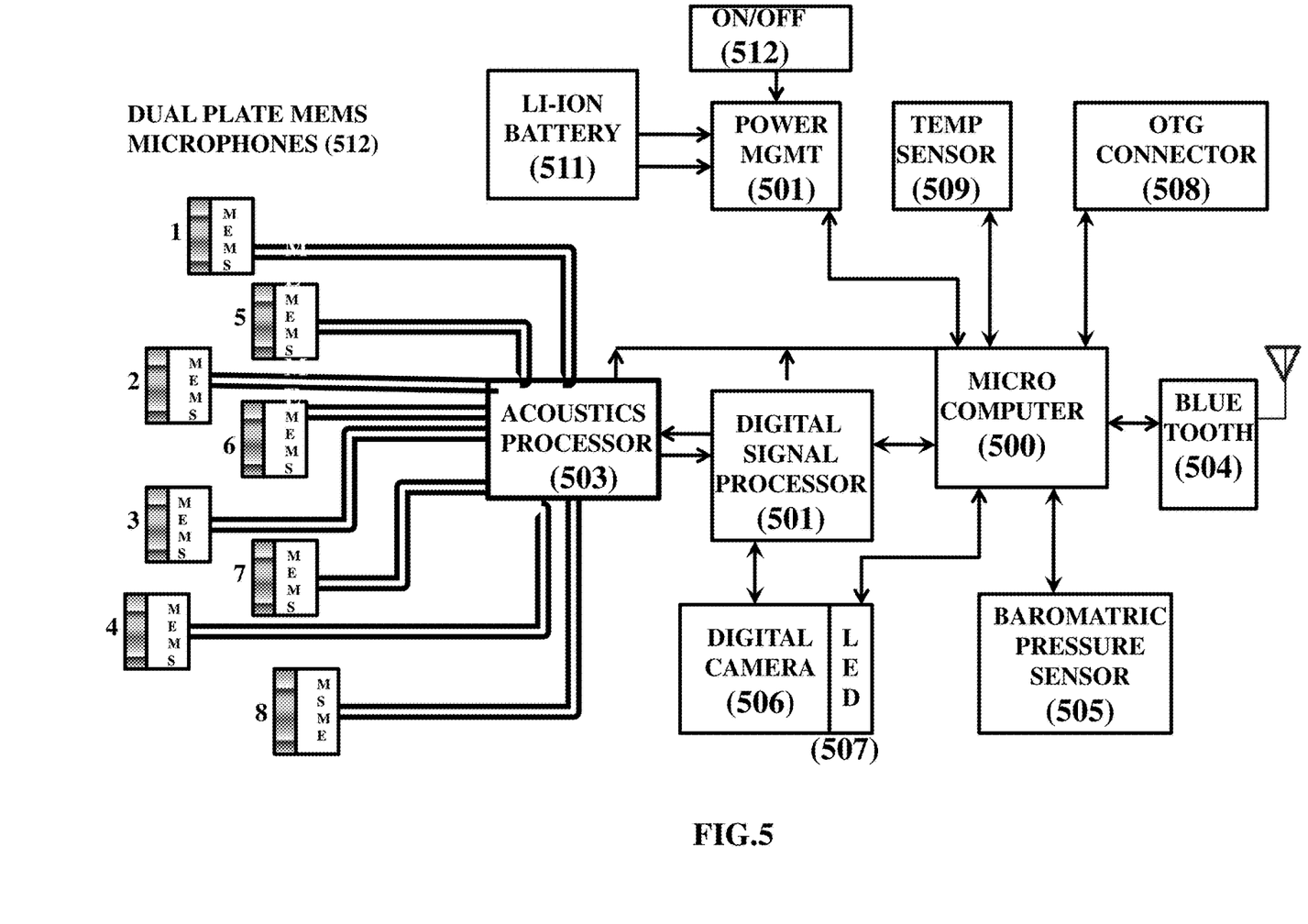
FIG. 5 shows block diagram of iDosT design

FIG. 5 of the invention gives a block diagram of the iDosT (101) design. Eight Dual-Plate digital MEMS microphones with pulse digital modulation (PDM) outputs are connected to Acoustics Processor (502) from XMOS. The dual plate digital MEMS microphones cancel the background noise and thus eliminating need for noise cancellation in the Digital Processor (502). The Processor (502) converts PDM stream to linear for digital signal processing. It has truly independent keyword trigger voice detection-lung, heart, abdomen, ear, nose, throat, temp. etc. to allow iDosT (101) to be configured in these modes by the user such as a physician. It can also be switched in these modes by the command from a Patient App (100) or PCP App (114). Additional digital processing for heart sound subtraction from lung sound, such as Kalman Filtering, or step Fast Fourier Transforms, are performed if needed in the DSP (501). Digital Camera (506) is used to scan ear, nose and other body parts as needed. The Processor (501) and (502) are connected to Microphones (500) on an I$^2$s bus. A MEMS Based digital Barometric Sensor (505) is used to measure patient's height, and also track motion of iDosT (101) during lung, abdomen, and heart auscultation. This Sensor (505) detects iDosT movement laterally and vertically during Lung, Heart, Abdomen Auscultation to make sure patient is positioning iDosT as per the physicians direction shown in the picture of App (100) (114). The microphone sound is substituted with silent sound during iDosT (101) movements to avoid discomfort in the physician's ear as well as noise in Medical Assistant's predictive algorithms.

Digital Camera (506) is used to observe patients inner ear, throat, nose using a cone shaped lens attachment, and LED (507) is to illuminate these organs. The physician can control intensity of the LED light remotely. The camera (506) is also used to check any skin discoloration and rashes on the patient's body. The LED (507) along with Camera (506) is used to check patient's eye movements. Temperature Sensor (509) is mounted on the tip of a cone shape device with connector which is screwed in the body of iDosT (101). It gets power and connected to its driver and analog to digital converter for patient's temperature measurement. Power Management Device (510) is used to power iDosT (101) electronics, and charge LI-ION battery. An ON/OFF switch (512) controls power to the device. The OTG Connector (508) is used to connect additional medical devices to the iDosT (101). Bluetooth module (504) is the preferred wireless communication means with the smartphone/tablet/laptop App (100) and App (114). All the components in the design are mounted on the PCB (403) using chip-on-board technology to achieve right form factor.

Microcomputer (500) controls all the peripheral devices and communicates with the App (100) or App (114) running at the patient and physicians location on their smartphone/tablet/laptop.

An algorithm similar to Kalman Filtering is used, using microphone sound with the motion and height detection using barometric sensor, to position the iDosT (101) at the optimum locations during lung, heart, and abdomen auscultations for the remote physician to listen to best sound. And this location is shown turning 'green' at the auscultation point in the PCP App (114) and Patient App (100). The physician can also remotely turn on, one at a time all the eight microphones to further enhance his diagnostics. The physician can control selectively any of the eight microphones. The physician can turn ON/OFF camera, thermometer LED Flash remotely. These remote control functions can be activated in iDosT by voice, touch icons on App (100) and App (114). The Patient App (100) will show these functions on the patient's body diagram as they are activated by the physician from PCP (114) App.

What is claimed is:

1. A Web Server based digital health care practice system which allows a patient to be seen remotely by a physician or a virtual physician, the system comprising:
    a smart compact pocketable integrated wireless digital device comprising;
        a digital camera for examining eyes, ear and throat,
        a digital thermometer,
        a digital MEMS barometric sensor configured to measure the patient's height, and motion of the smart compact pocketable integrated wireless digital device such that an optimum position of the smart compact pocketable integrated wireless digital device on the patient is determined,
        eight dual plate digital MEMS microphones for body sound listening, wherein the microphones are arranged in two concentric circle with four of the eight MEMS microphones in each circle, wherein the four MEMS microphones on each circle are spaced ninety degrees apart from a center of each circle, where each dual plate digital MEMS microphone is configured to be remotely turned on and off,
        a digital processor configured to recognize and process keyword voice command,
        a separate digital signal processor for filtering heart sound during lung sound auscultation, and
        a microcomputer with embedded firmware that controls collection of data from the smart compact pocketable integrated wireless digital device;
    at least one physician server comprising a multi core single server or separate servers, the at least one physician server is configured to handle secure communications with a patient application and a physician application and includes at least one of crypto technology, authentication using digital face and age, digital voice and finger print recognition, and password with one time password matching, the at least one physician server is configured to maintain calendars for patient's remote and in office visits, a home location register and visitor location register of the patient, the at least one physician server is configured to perform voice and video conferencing, virtual reality, virtual reality based examination scripts, voice and video text, email messaging and text alerts, and the at least one physician server is further configured to connect and communicate with home and visiting patient's billing application, pharmacy application, insurance billing, global patient's bill reconciliation, and data analytic tools, the at least one physician server further includes a medical assistant server which includes analytical tools using mathematical analysis to assist with diagnosis, picture and sound records during examination, the medical assistant server is configured to provide an independent diagnosis of the patient, a prescription assistant configured to suggest possible medicine for the patient and a symptom assistant that is configured to run a virtual reality examination;
    a data base system to store, retrieve, and archive data associated with the web server based digital health care practice system;
    the physician application is configured to run on a smartphone, a tablet, a laptop, or a desktop and allows the physician to give an examination in the physician's office or a remote location by connecting with the at least one physician server, the data base system and the compact pocketable integrated wireless digital device, the physician application is configured to control the smart compact pocketable integrated wireless digital device; and
    the patient application is configured to run on a smartphone, a tablet, a laptop, or a desktop and allows the patient to connect with the at least one physician server, the data base system and the compact pocketable integrated wireless digital device, the patient application is configured to control the smart compact pocketable integrated wireless digital device based on commands received from the physician application.

* * * * *